United States Patent [19]

Nishikawa et al.

[11] Patent Number: 4,661,352
[45] Date of Patent: Apr. 28, 1987

[54] WS 7739 SUBSTANCES, THEIR PREPARATION AND PHARMACEUTICAL COMPOSITION CONTAINING THE SAME

[75] Inventors: Motoaki Nishikawa, Toyonaka; Morita Iwami, Takarazuka; Keizo Yoshida, Suita; Masanobu Kohsaka, Sakai, all of Japan

[73] Assignee: Fujisawa Pharmaceutical Co., Ltd., Osaka, Japan

[21] Appl. No.: 662,927

[22] Filed: Oct. 19, 1984

[30] Foreign Application Priority Data

Nov. 15, 1983 [GB] United Kingdom ................. 8330465

[51] Int. Cl.$^4$ .......................... A61K 35/74; C12P 1/06
[52] U.S. Cl. ..................................... 424/117; 435/169
[58] Field of Search ................. 424/115, 117; 435/169

[56] References Cited

PUBLICATIONS

The Journal of Antibiotics, vol. XXXIX, No. 2, 1986, pp. 198–204, Japan Antibiotics Research Association, Okamoto et al: "A Specific Antagonist of Platelet Activating Factor (PAF) Produced by *Streptomyces phaeofaciens*.

*Primary Examiner*—Jerome D. Goldberg
*Attorney, Agent, or Firm*—Oblon, Fisher, Spivak, McClelland & Maier

[57] ABSTRACT

This invention relates to a biologically active WS-7739-A substance and a biologically active WS-7739-B substance which have pharmacological activities and are useful for the treatment of asthma, thrombosis and the alike.

4 Claims, No Drawings

WS 7739 SUBSTANCES, THEIR PREPARATION AND PHARMACEUTICAL COMPOSITION CONTAINING THE SAME

This invention relates to novel substances having pharmacological activity, hereinafter referred to WS 7739 substances. More particularly, this invention relates to a new biologically active WS 7739-A substance and a new biologically active WS 7739-B substance, which have pharmacological activities, to processes for their preparation and pharmaceutical compositions containing the same.

Accordingly, it is one object of this invention to provide novel compounds, WS 7739 substances having pharmacological activity.

Another object of this invention is to provide processes for preparing of the WS 7739 substances by fermentation of a WS 7739 substances-producing strain belonging to the genus Streptomyces in a nutrient medium.

A further object of this invention is to provide pharmaceutical compositions containing, as an active ingredient, the WS 7739 substances.

Still further object of this invention is to provide a method using WS 7739 substances for the treatment of asthma, thrombosis and the like.

The WS 7739 substances of this invention can be produced by fermentation of WS-7739 substances-producing strain belonging to the genus Streptomyces such as *Streptomyces phaeofaciens* No. 7739.

Particulars of microorganism used for preparing WS 7739 substances will be explained in the following.

THE MICROORGANISM

Strain No. 7739 was isolated from a soil sample obtained from Matsue-shi, Shimane-ken.

The methods described by Shirling and Gottlieb (Shirling, E. B. and D. Gottlieb: Methods for characterization of Streptomyces species. Int. J. Syst. Bacteriol. 16, 313-340, 1966) were employed principally for this taxonomic study. Morphological observations were made with light and electron microscopes on cultures grown at 30° C. for 14 days on yeast-malt extract agar, oatmeal agar or inorganic salts-starch agar. The mature spores occurred in chains of more than 30 spores forming spirals. The spores were cylindrical or oval and 0.7-1×0.6-0.75 μm in size by electron microscopic observation. Spore surfaces were smooth.

Cultural characteristics were observed on ten kinds of media described by Shirling and Gottlieb (Shirling, E. B. and D. Gottlieb: Methods for characterization of Streptomyces species. Int. J. Syst. Bacteriol. 16, 313-340, 1966), and by Waksman (Waksman, S. A.: The actinomycetes, vol. 2: Classification, identification and description of genera and species. The Williams and Wilkins Co., Baltimore, 1961).

The incubation was made at 30° C. for 14 days. The color names used in this study were based on Color Standard (published by Nihon Shikisai Co., Ltd.). Colonies belonged to the gray color series when grown on oatmeal agar, yeast-malt extract agar and inorganic salts-starch agar. No soluble pigment was produced in yeast-malt extract agar and others. Results were shown in Table 1.

TABLE 1

Cultural characteristics of strain No. 7739, *Streptomyces olivochromogenes* IFO 3292 and *Streptomyces pfaeofaciens* IFO 13372

| Medium | | Cultural characteristics | | |
| --- | --- | --- | --- | --- |
| | | No. 7739 | IFO 3292 | IFO 13372 |
| oatmeal agar | growth | poor | poor | poor |
| | aerial mass color | pale reddish brown | grayish white | light gray |
| | reverse side color | colorless | pale yellow | colorless |
| | soluble pigment | none | none | none |
| yeast-malt extract agar | growth | abundant | moderate | moderate |
| | aerial mass color | pale reddish brown | grayish white | pale reddish brown |
| | reverse side color | pale yellowish brown to black | light brown | pale yellowish brown |
| | soluble pigment | none | none | none |
| inorganic salts-starch agar | growth | abundant | abundant | abundant |
| | aerial mass color | light gray | grayish white | pale reddish brown |
| | reverse side color | gray to dark gray | pale yellow orange | pale yellow |
| | soluble pigment | none | none | none |
| glucose-asparagine agar | growth | moderate | abundant | moderate |
| | aerial mass color | gray | light gray | pale reddish brown |
| | reverse side color | pale yellow | dark brown | pale yellow |
| | soluble pigment | none | none | none |
| glycerin-asparagine agar | growth | abundant | abundant | abundant |
| | aerial mass color | grayish yellow brown | grayish white | pale reddish brown |
| | reverse side color | pale yellow | light brown | pale yellow |
| | soluble pigment | none | none | none |
| sucrose-nitrate agar | growth | poor | poor | poor |
| | aerial mass color | grayish white | none light gray | |
| | reverse side color | colorless | colorless | colorless |
| | soluble pigment | none | none | none |
| nutrient agar | growth | moderate | moderate | poor |
| | aerial mass color | light gray, scant | none | none |
| | reverse side color | pale yellow | pale yellow | colorless |
| | soluble pigment | none | none | none |

TABLE 1-continued

Cultural characteristics of strain No. 7739, Streptomyces olivochromogenes IFO 3292 and Streptomyces pfaeofaciens IFO 13372

| Medium | Cultural characteristics | No. 7739 | IFO 3292 | IFO 13372 |
|---|---|---|---|---|
| potato-dextrose agar | growth | poor | moderate | poor |
| | aerial mass color | none | grayish white | none |
| | reverse side color | colorless | pale brown | pale yellow orange |
| | soluble pigment | none | none | none |
| tyrosine agar | growth | abundant | moderate | abundant |
| | aerial mass color | pale yellow orange to gray | light gray | grayish white |
| | reverse side color | dark brown | yellowish brown | brown |
| | soluble pigment | dark brown | brown | brown |
| peptone-yeast extract-iron agar | growth | poor | moderate | moderate |
| | aerial mass color | none | none | none |
| | reverse side color | pale yellow | pale yellow | colorless |
| | soluble pigment | brown | brown | dark brown |

The cell wall analysis was performed by the methods of Becker et al. (Becker, B., M. P. Lechevalier, R. E. Gordon and H. A. Lechevalier: Rapid differentiation between Nocardia and Streptomyces by paper chromatography of whole-cell hydrolysates: Appl. Microbiol., 12 421-423, 1964) and Yamaguchi (Yamaguchi, T.: Comparison of the cell-wall composition of morphologically distinct actinomycetes: J. Bacteriol., 89 444-453, 1965). Analysis of whole cell hydrolysates of strain No. 7739 showed that it contained LL-diaminopimeric acid. Accordingly, the cell wall of this strain was believed to be of type I.

Physiological properties of strain No. 7739 were shown in Table 2. Temperature range and optimum temperature for growth were determined on yeast-malt extract agar using a temperature gradient incubator (made by Toyo Kagaku Sangyo Co., Ltd.). Temperature range for growth was from 7° C. to 38° C. with optimum from 27° to 32° C. Starch hydrolysis, melanin production, gelatin liquefaction and urease activity were positive.

TABLE 2

Physiological properties of strain No. 7739, Streptomyces olivochromogenes IFO 3292 and Streptomyces phaeofaciens IFO 13372

| Physiological properties | No. 7739 | IFO 3292 | IFO 13372 |
|---|---|---|---|
| Temperature range for growth | 7° C.-38° C. | 16° C.-36° C. | 11° C.-36° C. |
| Optimum temperature | 27° C.-32° C. | 27° C. | 25° C.-27° C. |
| Nitrate reduction | negative | negative | positive |
| Starch hydrolysis | positive | positive | negative |
| Milk coagulation | negative | positive | negative |
| Milk peptonization | negative | positive | positive |
| Melanin production | positive | positive | positive |
| Gelatin liquefaction | positive | positive | negative |
| $H_2S$ production | negative | negative | negative |
| Urease activity | positive | positive | positive |
| NaCl tolerance (%) | <7% | <10% | <7% |

Utilization of carbon sources was examined according to the methods of Pridham and Gottlieb (Pridham, T. G. and D. Gotlieb: The utilization of carbon compounds by some Actinomycetales as an aid for species determination: J. Bacteriol. 56, 107-114(1948). The results were determined after 14 days incubation at 30° C. Almost all sources were utilized except cellulose and chitin.

Summarized carbon sources utilization of this strain is shown in Table 3.

TABLE 3

Carbon utilization of strain No. 7739, Streptomyces olivochromogenes IFO 3292 and Streptomyces phaeofaciens IFO 13372

| Carbon sources | No. 7739 | IFO 3292 | IFO 13372 |
|---|---|---|---|
| D-glucose | + | + | + |
| sucrose | + | − | − |
| glycerin | + | + | + |
| D-xylose | + | − | ± |
| D-fructose | + | − | + |
| lactose | + | + | + |
| maltose | + | + | + |
| rhamnose | + | − | + |
| raffinose | + | + | − |
| D-galactose | + | + | + |
| L-arabinose | + | ± | + |
| D-mannose | + | + | + |
| D-trehalose | + | + | + |
| inositol | + | − | + |
| D-mannitol | + | − | + |
| inulin | + | − | − |
| cellulose | − | − | − |
| salicin | + | − | + |
| chitin | − | − | − |
| sodium citrate | + | − | + |
| sodium succinate | + | + | + |
| sodium acetate | + | − | − |

Symbols:
+: utilization
±: doubtful utilization
−: no utilization

Microscopic studies and cell wall composition analysis of this strain indicate that this strain belongs to the genus Streptomyces Waksman and Henrici 1943. Accordingly, a comparison of this strain was made with the published description (Shirling, E. B. and D. Gottlieb: Cooperative description of type culture of Streptomyces. 2: Species descriptions from first study. Intern. J. Syst. Bacteriol. 18, 69-189, 1968; Shirling, E. B. and D. Gottlieb: Cooperative description of type cultures of Streptomyces. 3.: Additional species description from first and second studies. Intern. J. Syst. Bacteriol., 18, 279-392, 1968; Shirling, E. B. and D. Gottlieb: Cooperative description of type cultures of Streptomyces. 4. Species descriptions from the second, third and fourth studies. Intern. J. Syst. Bacteriol. 19, 391-512, 1969 and Buchanan, R. E. and N. E. Gibbons: Bergey's Manual of Determinative Bacteriology, 8th edition. The Williams and Wilkins Co., Baltimore, 1974) of various Streptomyces species. Strain No. 7739 is considered to resemble *Streptomyces olivochromogenes* (Waksman 1923) Waksman and Henrici 1948 and *Streptomyces phaeofaciens* Maeda, Okami, Taya and Umezawa 1952. These two species were differentiated from strain No. 7739 in the following points.

*Streptomyces olivochromogenes* IFO 3292

Aerial mass color of *Streptomyces olivochromogenes* is different from that of strain No. 7739 on glucose-asparagine agar, glycerin-asparagine agar and potato-dextrose agar. Reverse side color of *Streptomyces olivochromogenes* is different from that of strain No. 7739 on glucose-asparagine agar, glycerin-asparagine agar and potato-dextrose agar. Milk coagulation, milk peptonization and 7% NaCl tolerance are positive. *Streptomyces olivochromogenes* can not assimilate sucrose, D-xylose, D-fructose, rhamnose, inositol, D-mannitol, inulin, salicin, sodium citrate and sodium acetate.

*Streptomyces phaeofaciens* IFO 13372

Cultural characteristics of *Streptomyces phaeofaciens* resemble the strain No. 7739. Nitrate reduction and milk peptonization are positive. Starch hydrolysis and gelatin liquefaction are negative. Streptomyces phaeofaciens can not assimilate sucrose, raffinose, inulin and sodium acetate.

Cultural characteristics of the strain No. 7739 are in good agreement with those of *Streptomyces phaeofaciens*. However, physiological properties and carbon sources utilization of the strain No. 7739 is different from *Streptomyces phaeofaciens* in the several points. These differences do not seem to us sufficient to distinguish strain No. 7739 from *Streptomyces phaeofaciens*. Therefore, strain No. 7739 is considered a new subspecies of *Streptomyces phaeofaciens* and the strain has been designated as *Streptomyces phaeofaciens* subsp. *matsuenensis* subsp. nov., referring to the soil obtained at Matsue-shi from which the organism was isolated.

A culture of the *Streptomyces phaeofaciens* subsp. *matsuenensis* No. 7739 has been deposited with Fermentation Research Institute Agency of Industrial Science and Technology (Japan) under the number of FERM BP-660 (deposit date: Oct. 31, 1983).

PRODUCTION OF WS 7739 SUBSTANCES

The WS 7739 substances of this invention is produced when a WS 7739 substances-producing strain belonging to the genus Streptomyces (e.g. *Streptomyces phaeofaciens* subsp. *matsuenensis* No. 7739 FERM P-7322) is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, sucrose, glycerin, starch and the like. Other sources which may be included are xylose, galactose, maltose, dextrin, lactose and the like.

The preferred sources of nitrogen are yeast extract, peptone, gluten meal, cottonseed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea, amino acid and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as calcium carbonate, sodium or potassium phosphate, sodium or potassium chloride, magnesium salts, copper salts and the like. If necessary, especially when the culture medium foams seriously a defoaming agent, such as liquid paraffin, fatty oil, plant oil, mineral oil or silicone may be added.

As in the case of the preferred methods used for the production of other biologically active substances in massive amounts, submerged aerobic cultural conditions are preferred for the production of WS 7739 substances in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the WS 7739 substances. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the WS 7739 substances.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Agitation may be effected by passing sterile air through the fermentation mixture.

The fermentation is usually conducted at a temperature between about 20° C. and 40° C., preferably 25°–35° C., for a period of about 50 hours to 150 hours.

Thus produced WS 7739 substances can be recovered from the culture medium by conventional means which are commonly used for the recovery of other known biologically active substances.

In general, most of the WS 7739 substances produced are found in the cultured broth, and accordingly the WS 7739 substances can be separated from the filtrate, which is obtained by filtering or centrifuging the culture broth, by a conventional method such as concentration under reduced pressure, lyophilization, pH adjustment, treatment with a resin (e.g. anion or cation exchange resin, non-ionic adsorption resin), treatment with a conventional adsorbent (e.g. activated carbon, silicic acid, silica gel, cellulose, alumina), gel filtration, crystallization, and the like.

The WS 7739 substances obtained according to the aforementioned process possesses the following physical and chemical properties.

WS 7739-A substance (1) Form and color: pale yellow powder (2) Elementary analysis: C: 63.89%, H: 7.09%, N: 9.83%, S: 7.53%.

(3) Color reaction:

Positive: Cerium sulfate reaction, iodine reaction, Ehrlich reaction, Dragendorff reaction and phosphomolybdic acid reaction Negative: ninhydrin reaction (4) Solubility:

Soluble: methanol, ethanol, acetone, ethyl acetate

Slightly soluble: benzene

Insoluble: hexane, water (5) Melting point: 100°–105° C.

(6) Specific rotation: $[\alpha]_D^{23} = +98.0°$ (c=1.0, CHCl$_3$).

(7) Ultraviolet absorption spectrum:

$\lambda_{max}^{Methanol} = 252$ nm($E_{1\ cm}^{1\%} = 5290$)

$= 332$ nm($E_{1\ cm}^{1\%} = 8920$)

$\lambda_{max}^{Methanol + HCl} = 252, 332$ nm $\lambda_{max}^{Methanol + NaOH} = 244, 340$ nm (8) Infrared absorption spectrum:
$\nu_{max}^{CHCl_3} = 3380, 3000, 2930, 1700(sh), 1675, 1615, 1595, 1500, 1475, 1450, 1380, 1355, 1310, 1300, 1130, 1095, 1020$ cm$^{-1}$.

(9) Molecular weight: EIMS: m/z 413 (M+).

(10) $^{13}$C Nuclear magnetic resonance spectrum (CDCl$_3$):
δ(ppm): 206.1, 176.1, 168.1, 151.2, 144.4, 128.4, 127.3, 123.2, 123.1, 108.5, 105.4, 56.4, 54.5, 46.1, 44.5, 39.3, 39.3, 28.9, 26.2, 21.3, 16.8, 12.8.

(11) $^1$H Nuclear magnetic resonance spectrum (CDCl$_3$):
δ(ppm): 10.3(1H, d, J=5 Hz), 7.38(1H, d, J=4.6 Hz), 7.32(1H, br. t, J=7.5 Hz), 7.13(1H, d, J=7.5 Hz), 7.08(1H, t, J=7.5 Hz), 6.87(1H, d, J=7.5 Hz), 4.53(1H, dd, J=10 and 4.6 Hz), 4.25(1H, m), 3.93(1H, d, J=4 Hz), 3.22(3H, s), 3.11(1H, dd, J=14 and 4 Hz), 3.00(1H, dd, 14 and 7.3 Hz), 2.98(1H, m), 2.63(1H, m), 2.53(1H, m), 2.38-2.32(2H, m), 2.23(3H, s), 1.90(1H, m), 1.83(1H, m), 0.72(3H, d, J=6.8 Hz).

WS 7739-B substance (1) Form and color: pale yellow powder
(2) Elementary analysis: C: 63.22%, H: 6.10%, N: 9.97%, S: 8.30%
(3) Color reaction:
Positive: Cerium sulfate reaction, iodine reaction, Ehrlich reaction, Dragendorff reaction and phosphomolybdic acid reaction
Negative: ninhydrin reaction
(4) Solubility:
Soluble: methanol, ethanol, acetone, ethyl acetate
Slightly soluble: benzene
Insoluble: hexane, water
(5) Melting point: 112°-120° C.
(6) Specific rotation: $[\alpha]_D^{23} = +97.0°$ (c=0.5, CHCl$_3$).
(7) Ultraviolet absorption spectrum:

$\lambda_{max}^{Ethanol} = 246$ nm($E_{1\ cm}^{1\%} = 362$)

$= 347$ nm($E_{1\ cm}^{1\%} = 347$)

$\lambda_{max}^{Ethanol + HCl} = 246, 347$ nm $\lambda_{max}^{Ethanol + NaOH} = 295, 330$ nm (8) Infrared absorption spectrum:
$\nu_{max}^{CHCl_3} = 3350, 3000, 2900, 1670, 1610, 1595, 1490, 1470, 1445, 1380, 1350, 1340, 1310, 1297, 1220, 1120, 1110, 1085, 1020, 920$ cm$^{-1}$.

(9) Molecular weight: EIMS: m/z 411 (M+).

(10) $^{13}$C Nuclear magnetic resonance spectrum (CDCl$_3$):
δ(ppm): 196.8, 176.1, 168.1, 151.0, 150.1, 144.4, 136.3, 128.4, 127.3, 123.2, 123.1, 108.4, 104.9, 56.8, 54.9, 46.0, 44.2, 39.2, 34.5, 26.2, 16.9, 13.2.

(11) $^1$H Nuclear magnetic resonance spectrum (CDCl$_3$):
δ(ppm): 10.18(1H, d, J=5 Hz), 7.18(1H, d, J=4.6 Hz), 7.4-7.0(4H, m), 6.87(1H, d, J=7.8 Hz), 6.34(1H, td, J=5.9 and 2.0 Hz), 4.50(1H, ddd, J=10.2, 4.6 and 1.4 Hz), 4.33(1H, m), 3.97(1H, d, J=3.9 Hz), 3.24(3H, s), 3.22(2H, m), 3.11(2H, m), 2.98(1H, m), 2.27(3H, s), 0.72(3H, d, J=6.8 Hz).

BIOLOGICAL PROPERTIES OF THE WS 7739 SUBSTANCES

The WS 7739 substances is useful for the treatment of asthma, thrombosis and the like.

As an example for showing such pharmacological activity, some pharmacological test data are illustrated in the following.

TEST 1

Inhibition of platelet aggregation

Blood was collected through the polyethylene catheter introduced into the carotid artery of male Japanese white rabbit (2.5 to 3 kg body weight). The blood was anticoagulated with 1 volume of 3.8% sodium citrate to 9 volume of blood. Platelet rich plasma (PRP) was prepared by centrifugation of the blood at 150 g for 10 minutes in room temperature. The PRP was diluted with platelet poor plasma obtained by further centrifugation of the blood at 1,000 g for 20 minutes. The platelet number was $5 \times 10^5$ cells/mm$^3$. Aggregometry was performed with platelet aggregating agents in a NKK Hema Tracer (Niko Bioscience Inc.) at 37° C., using 0.3 ml combined volume of PRP and reagents in a cylindrical glass cuvette under constant stirring with a magnetic stirring bar (1,000 rpm). Platelet aggregation was measured turbidmetrically by recording changes of the light transmission of PRP during aggregation.

Activities of inhibitors were expressed as IC$_{50}$ value, i. e. concentrations required to inhibit the platelet aggregation response by 50%. Arachidonic acid was used at the final concentration of 150 μM. The final concentration of platelet-activating factor (hereinafter referred to PAF) and thrombin, usually 20 nM and 0.8 u/ml, respectively, was chosen to induce approximately 75% of the maximum aggregation.

The result is shown in Table 4.

TABLE 4

| Inhibitory activity of WS 7739 substances against rabbit platelet aggregation | | |
|---|---|---|
| | IC$_{50}$ value of WS 7739 substances (μg/ml) | |
| Inducers | WS 7739-A | WS 7739-B |
| PAF | 0.076 | 0.046 |
| arachidonic acid | 8< | 8< |
| thrombin | 8< | 8< |

TEST 2

Inhibition of brocho-constriction induced by intravenously injected PAF in guinea pigs Male guinea pigs (Hartley) weighing 300-500 g were used. These guinea pigs were anesthetized with gallamine triethiodide intraperitoneally at a dose of 20 mg/kg. Tracheae were cannulated and the animals were artificially ventilated by a positive pressure pump at 60 strokes/min with 5 ml/stroke. Changes in pressure were measured by connecting a side arm from the tracheal cannula to a rpessure transducer coupled to a Biophysiograph 180 System ((San-Ei Instrument Co., Ltd.). A catheter was introduced into the right jugular vein for the administration of drugs. The increase of pulmonary pressure induced by intravenously injected synthetic PAF (1 μg/kg) was measured and the efficacy of the drug was shown in Table 5 as the inhibition percentage of the pressure increase. Drugs were administered intravenously 10 minutes before PAF injection.

TABLE 5

Effect of WS 7739-B substance to bronchospasm induced by PAF in guinea pig

| | N = | Increase in pulmonary pressure $\Delta p$(mm $H_2O$) $\bar{x} \pm SE$ | inhibition % |
|---|---|---|---|
| vehicle | 6 | 31.67 ± 3.68 | |
| WS 7739-B substance | | | |
| 1 mg/kg | 3 | 21.0 ± 7.37 | 34 |
| 10 mg/kg | 3 | 0 | 100* |

*p < 0.001

TEST 3

Inhibition of hypotensive effect induced by intravenously injected PAF in rats

Seven-weeks old Sprague-Dowley rats were anesthetized with urethane (700 mg/kg, i. p.). Catheters were introduced into the femoral artery and vein for the measurement of arterial pressure and the administration of drugs, respectively. Blood pressure was recorded from femoral artery using a transducer coupled to the Biophysiograph 180 System (San-Ei Instrument Co., Ltd.) Inhibitory activity of test drugs was shown in Table 6 as the inhibition percentage of the synthetic PAF induced hypotension. PAF was administered intravenously at a dose of 1 μg/kg. Drugs were administered intravenously 3 minutes before PAF injection.

TABLE 6

Effect of WS 7739-B substance to hypotension induced by PAF in rat

| | N = | Decrease in mean arterial blood pressure $\Delta p$(mm Hg) $\bar{x} \pm SE$ | inhibition % |
|---|---|---|---|
| vehicle | 8 | 58.1 ± 3.0 | — |
| WS 7739-B substance | | | |
| 0.3 mg/kg | 3 | 53.3 ± 4.4 | 8 |
| 1 mg/kg | 3 | 25.0 ± 7.6 | 57** |
| 10 mg/kg | 4 | 2.5 ± 2.5 | 96** |

**p < 0.001

The pharmaceutical composition of this invention can be used in the form of a pharmaceutical preparation, for example, in solid, semisolid or liquid form, which contains WS 7739 substances, as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing thickening and coloring agents and perfumes may be used. The active object compound is included in the pharmaceutical composition in an amount sufficient to produce the desired effect upon the process or condition of diseases.

For applying this composition to human, it is preferably to apply it by oral administration. While the dosage or therapeutically effective amount of the WS 7739 substances varies from and also depends upon the age and condition of each individual patient to be treated, a daily dose of about 0.1–100 mg, preferably 0.5–5 mg, of the active ingredient/kg of a human being is generally given for treating diseases, and an average single dose of about 5 mg, 10 mg, 50 mg, 100 mg, 250 mg and 500 mg is generally administered.

The following examples are given for the purpose of illustrating the present invention.

EXAMPLE 1

Preparation of WS 7739-A substance

Fermentation:

Seed medium (80 ml) containing corn starch (1%), glycerin (1%), glucose (0.5%), dry yeast (0.5%), %), corn steep liquor (0.5%), cotton seed flour (1%) (adjusted to pH 6.5 with 6N NaOH) and $CaCO_3$ (0.2%) was poured into each of twenty-five 250 ml-Erlenmeyer flasks and sterilized at 120° C. for 30 minutes. A loopful of slant culture of *Streptomyces phaeofaciens* subsp. *matsuenensis* No. 7739 FERM P-7322 was inoculated to each of the media and cultured at 30° C. for 72 hours on a rotary shaker with 3-inch throw at 220 rpm. The resultant seed culture was inoculated to a production medium (160 liters) containing glycerin (1%), glutenmeal (0.7%), $(NH_4)_2SO_4$ (0.1%), $MgSO_4.7H_2O$ (0.05%), $CaCO_3$ (0.2%), $COCl_2.6H_2O$ (4 μg/ml) and NaI (0.5 μg/ml) in a 200 liter stainless steel fermentor which had been sterilized at 120° C. for 30 minutes and cultured at 30° C. for 96 hours under aeration of 160 liters/min and agitation of 200 rpm.

Isolation:

The cultured broth thus obtained was filtered with an aid of diatomaseous earth. The filtrate (160 liters) was adjusted to pH 7.0 and then extracted with 160 liters of ethyl acetate.

The extract was concentrated in vacuo. The resultant material was applied to a silica gel column chromatography (1.5 liters) and the column was eluted with a mixture of n-hexane-acetone(1:1). The fractions containing active compound were applied to pre-packed column (Lichroprep Si 60 size B, Merck) and eluted with a mixture of chloroform-methanol(100:1). WS 7739-A substance was eluted in advance of WS 7739-B substance. The active fractions containing WS 7739-A substance were rechromatographed using pre-packed column with the same condition. The active fraction were concentrated in vacuo to give 230 mg pure powder of WS 7739-A substance.

EXAMPLE 2

Preparation of WS 7739-B substance

Fermentation:

Seed medium (80 ml) containing corn starch (1%), glycerin (1%), glucose (0.5%), dry yeast (0.5%), %), corn steep liquor (0.5%), cotton seed flour (1%) (adjusted to pH 6.5 with 6N NaOH) and $CaCO_3$ (0.2%) was poured into each of twenty-five 250 ml-Erlenmeyer flasks and sterilized at 120° C. for 30 minutes. A loopful of slant culture of *Streptomyces phaeofaciens* subsp. *mat-*

*suenensis* No. 7739 FERM P-7322 was inoculated to each of the media and cultured at 30° C. for 72 hours on a rotary shaker with 3-inch throw at 220 rpm. The resultant seed culture was inoculated to a production medium (160 leters) containing glycerin (1%), glutenmeal (0.7%), $(NH_4)_2SO_4$ (0.1%), $MgSO_4.7H_2O$ (0.05%), $CaCO_3$ (0.2%), $CoCl_2.6H_2O$ (4 μg/ml) and NaI (0.5 μg/ml) in a 200 liter stainless steel fermentor which had been sterilized at 120° C. for 30 minutes and cultured at 30° C. for 96 hours under aeration of 160 liters/min and agitation of 200 rpm.

Isolation:

The cultured broth thus obtained was filtered with an aid of diatomaseous earth. The filtrate (160 liters) was adjusted to pH 7.0 and then extracted with 160 liters of ethyl acetate.

The extract was concentrated in vacuo. The resultant material was applied to a silica gel column chromatography (1.5 liters) and the column was eluted with a mixture of n-hexane-acetone(1:1). The fractions containing active compound were applied to pre-packed column (Lichroprep si 60 size B, Merck) and eluted with a mixture of chloroform-methanol(100:1). WS7739-B substance eluted following WS 7739-A substance. The active fractions containing WS 7739-B substance were rechromatographed using pre-packed column with the same condition. The active fraction were concentrated in vacuo to give 300 mg pure powder of WS 7739-B substance.

What we claim is:

1. WS 7739 substances selected from the group consisting of WS 7739-A substance and WS 7739-B substance, wherein
   (i) the WS 7739-A substance has the following physical and chemical properties.
   (1) Form and color:
      pale yellow powder
   (2) Elementary analysis: C: 63.89%, H: 7.09%, N: 9.83%, S: 7.53%
   (3) Color reaction:
      Positive: Cerium sulfate reaction, iodine reaction, Ehrlich reaction, Dragendorff reaction and phosphomolybdic acid reaction
      Negative: ninhydrin reaction
   (4) Solubility:
      Soluble: methanol, ethanol, acetone, ethyl acetate
      Slightly soluble: benzene
      Insoluble: hexane, water
   (5) Melting point:
      100°–105° C.
   (6) Specific rotation:
      $[\alpha]_D^{23} = +98.0°$ (c=1.0, $CHCl_3$)
   (7) Ultraviolet absorption spectrum:

$$\lambda_{max}^{Methanol} = 252 \text{ nm}(E_{1\ cm}^{1\%} = 5290)$$
   $$= 332 \text{ nm}(E_{1\ cm}^{1\%} = 8920)$$
   $$\lambda_{max}^{Methanol + HCl} = 252, 332 \text{ nm}$$
   $$\lambda_{max}^{Methanol + NaOH} = 244, 340 \text{ nm}$$

(8) Infrared absorption spectrum:
      $\nu_{max}^{CHCl_3}$=3380, 3000, 2930, 1700(sh), 1675, 1615, 1595, 1500, 1475, 1450, 1380, 1355, 1310, 1300, 1130, 1095, 1020, $cm^{-1}$
   (9) Molecular weight:
      EIMS: m/z 413 ($M^+$)
   (10) $^{13}C$ Nuclear magnetic resonance spectrum ($CDCl_3$):
      δ(ppm): 206.1, 176.1, 168.1, 151.2, 144.4, 128.4, 127.3, 123.2, 123.1, 108.5, 105.4, 56.4, 54.5, 46.1, 44.5, 39.3, 39.3, 28.9, 26.2, 21.3, 16.8, 12.8
   (11) $^1H$ Nuclear magnetic resonance spectrum ($CDCl_3$):
      δ(ppm): 10.3(1H, d, J=5 Hz), 7.38(1H, d, J=4.6 Hz), 7.32(1H, br. t, J=7.5 Hz), 7.13(1H, d, J=7.5 Hz), 7.08(1H, t, J=7.5 Hz), 6.87(1H, d, J=7.5 Hz), 4.53(1H, dd, J=10 and 4.6 Hz), 4.25(1H, m), 3.93(1H, d, J=4Hz), 3.22(3H, s), 3.11(1H, dd, J=14 and 4 Hz), 3.00(1H, dd, 14 and 7.3 Hz), 2.98(1H, m), 2.63(1H, m), 2.53(1H, m), 2.38–2.32(2H, m), 2.23(3H, s), 1.90(1H, m), 1.83(1H, m), 0.72(3H, d, J=6.8 Hz)

or (ii) the WS 7739-B substance has the following properties:
   (1) Form and color:
      pale yellow powder
   (2) Elementary analysis:
      C: 63.22%, H:6.10%, N:9.97%, S: 8.30%
   (3) Color reaction:
      Positive: Cerium sulfate reaction, iodine reaction, Ehrlich reaction, Dragendorff reaction and phosphomolybdic acid reaction
      Negative: ninhydrin reaction
   (4) Solubility:
      Soluble: methanol, ethanol, acetone, ethyl acetate
      Slightly soluble: benzene
      Insoluble: hexane, water
   (5) Melting point:
      112°–120° C.
   (6) Specific rotation:
      $[\alpha]_D^{23} = +97.0°$ (c=0.5, $CHCl_3$)
   (7) Ultraviolet absorption spectrum:

$$\lambda_{max}^{Ethanol} = 246 \text{ nm}(E_{1\ cm}^{1\%} = 362)$$
   $$= 347 \text{ nm}(E_{1\ cm}^{1\%} = 347)$$
   $$\lambda_{max}^{Ethanol + HCl} = 246, 347 \text{ nm}$$
   $$\lambda_{max}^{Ethanol + NaOH} = 295, 330 \text{ nm}$$

(8) Infrared absorption spectrum:
      $\nu_{max}^{CHCl_3}$=3350, 3000, 2900, 1670, 1610, 1595, 1490, 1470, 1445, 1380, 1350, 1340, 1310, 1297, 1220, 1120, 1110, 1085, 1020, 920 $cm^{-1}$
   (9) Molecular weight:
      EIMS: m/z 411 ($M^+$)
   (10) $^{13}C$ Nuclear magnetic resonance spectrum ($CDCl_3$):
      δ(ppm): 196.8, 176.1, 168.1, 151.0, 150.1, 144.4, 136.3, 128.4, 127.3, 123.2, 123.1, 108.4, 104.9, 56.8, 54.9, 46.0, 44.2, 39.2, 34.5, 26.2, 16.9, 13.2
   (11) $^1H$ Nuclear magnetic resonance spectrum ($CDCl_3$):
      δ(ppm): 10.18(1H, d, J=5 Hz), 7.18(1H, d, J=4.6 Hz), 7.4–7.0(4H, m), 6.87(1H, d, J=7.8 Hz), 6.34(1H, td, J=5.9 and 2.0 Hz), 4.50(1H, ddd, J=10.2, 4.6 and 1.4 Hz), 4.33(1H, m), 3.97(1H, d, J=3.9 Hz), 3.24(3H, s), 3.22(2H, m), 3.11(2H, m), 2.98(1H, m), 2.27(3H, s), 0.72(3H, d, J=6.8 Hz).

2. A process for preparing WS 7739 substances selected from the group consisting of WS 7739-A substance and WS 7739-B substance as defined in claim 1 which comprises culturing a WS 7739 substance-producing strain belonging to the genus *Streptomyces phaeofaciens* No. 7739 FERM BP-660 in an aqueous nutrient medium under aerobic conditions until substantial pharmacological activity is imparted to said medium, and recovering the WS 7739-A substance or WS 7739-B substance or mixture thereof from the cultured medium.

3. A pharmaceutical composition comprising an effective antiasthmatic amount of WS 7739-A substance or WS 7739-B substance or mixture thereof as defined in claim 1 in association with a pharmaceutically acceptable, substantially non-toxic carrier excipient.

4. A pharmaceutical composition comprising an effective antithrombotic amount of WS 7739-A substance or WS 7739-B substance or mixture thereof as defined in claim 1 in association with a pharmaceutically acceptable, substantially non-toxic carrier or excipient.

* * * * *